United States Patent [19]
Daughenbaugh et al.

[11] Patent Number: 6,132,726
[45] Date of Patent: Oct. 17, 2000

[54] PROCESS FOR REMOVING IMPURITIES FROM NATURAL PRODUCT EXTRACTS

[75] Inventors: Randall J. Daughenbaugh, Longmont; David T. Bailey, Boulder; William R. Gamble, Boulder; Dennis D. Gertenbach, Boulder, all of Colo.

[73] Assignee: Hauser, Inc., Boulder, Colo.

[21] Appl. No.: 09/176,348

[22] Filed: Oct. 21, 1998

[51] Int. Cl.⁷ ................................................. A61K 35/78
[52] U.S. Cl. ........................................................ 424/195.1
[58] Field of Search .......................................... 424/195.1

[56] References Cited

U.S. PATENT DOCUMENTS

| | | | |
|---|---|---|---|
| 3,901,875 | 8/1975 | Park | 260/210.5 |
| 3,950,266 | 4/1976 | Chang et al. | |
| 4,317,816 | 3/1982 | Arichi et al. | |
| 4,361,697 | 11/1982 | Dobberstein et al. | |
| 4,610,790 | 9/1986 | Reti et al. | |
| 4,621,137 | 11/1986 | Miyake et al. | |
| 4,755,504 | 7/1988 | Liu | |
| 4,842,878 | 6/1989 | Forster et al. | 426/286 |
| 4,946,695 | 8/1990 | Forster et al. | 426/286 |
| 5,093,123 | 3/1992 | Schutz et al. | 424/195.1 |
| 5,137,878 | 8/1992 | Pang et al. | |
| 5,368,411 | 11/1994 | Losack | |
| 5,484,538 | 1/1996 | Woodward | |
| 5,585,505 | 12/1996 | Mulder et al. | |
| 5,660,832 | 8/1997 | Steiner et al. | 424/195.1 |
| 5,843,911 | 12/1998 | Nakahara et al. | |

OTHER PUBLICATIONS

VWR Scientific Catalog, pp. 652–653 and 655, 1989/90.
Fischer Scientific Catalog, pp. 1192–1197, 1988.

*Primary Examiner*—Christopher Tate
*Attorney, Agent, or Firm*—Hogan & Hartson LLP; Steven C. Petersen; Sarah S. O'Rourke

[57] ABSTRACT

In general the present invention relates to a process for the removal of undesireable compounds or residues from an extract which are more polar or less polar than the desired target compound. The preferred embodiment of the present invention is a three step process and is described in detail below. The first step includes contacting a plant material that contains the desired target compound(s) with a solvent, thus producing a crude extract containing a mixture of compounds that includes, in addition to the undesireable residues, the desired target compound(s). The second step involves passing the crude extract through a series of columns containing an absorbent that retards the movement of the undesireable compounds, while allowing the desired compounds to pass. The third and final step involves drying the eluant product to achieve a final product.

22 Claims, 3 Drawing Sheets

PROCESS FOR REMOVING IMPURITIES FROM NATURAL PRODUCT EXTRACTS

CROSS-REFERENCE TO DISCLOSURE DOCUMENTS

This patent application references Disclosure Document entitled "Removal of Pesticides from Ginseng," No.: 442467, filed Aug. 10, 1998.

BACKGROUND OF THE INVENTION

1. Field of the Invention

The present invention relates to a continuous process for separating organic compounds contained in an extract based on polarity. More particularly, the present invention relates to a commercial process whereby a target compound of interest may be purified by removing undesirable compounds that are more polar or less polar than the target compound.

2. Description of the State of Art

The word "Gin-seng" or "jen-shen" translates from Chinese to "essence of the earth in the form of a man" due to the root's resemblance to the human body. Its widespread use is based upon traditional medicine's belief that ginseng has a unique ability to promote a balance of body and spirit. While the genus Panax contains six species native to Asia and two native to North America, almost all of the commercially available *Panax ginseng* root is cultivated in the northeastern district and other regions of China and Korea.

Only the roots of *Panax ginseng* are used medicinally. The main root is a fleshy tap root, branched into smaller rootlets. At the age of 4 to 6 years, when most of the cultivated plants are harvested, their roots usually are about 2 to 3 centimeters in diameter and about 10 to 20 centimeters in length.

Research has identified several classes of compounds in *Panax ginseng* that are believed to act on the body in a number of beneficial ways. The ginsenosides, a family of saponins, are believed to be the most important. The ginsenosides are made up of two groups, Rg and Rb, each containing several related compounds. Studies have indicated that most of the physiologic effects of ginseng can be related to the ginsenosides.

The Rg group consists of derivatives of protopanaxatriol and includes $Rg_1$, Re, Rf, $Rg_2$, and several other related compounds. This group is believed to possess the stimulatory effect on the central nervous system.

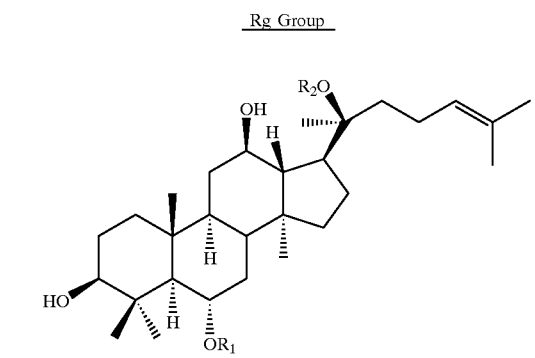

Rg Group

| Ginsenoside | $R_1$ | $R_2$ |
|---|---|---|
| $Rg_1$ | D-Glucose | D-Glucose |
| Re | L-Rhamnose-($\alpha$-1-2)-D-Glucose | D-Glucose |
| Rf | D-Glucose-($\beta$-1-2)-D-Glucose | H |
| $Rg_2$ | L-Rhamnose-($\alpha$-1-2)-D-Glucose | H |

The Rb group consists of derivatives of protopanaxadiol and includes $Rb_1$, $Rb_2$, Rc, Rd, and several other related compounds. This group is believed to possess the depressant effect on the central nervous system.

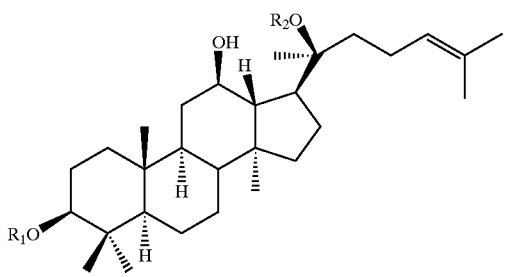

Rb Group

| Ginsenoside | $R_1$ | $R_2$ |
|---|---|---|
| $Rb_1$ | D-Glucose-($\beta$-1-2)-D-Glucose | D-Glucose-($\beta$-1-6)-D-Glucose |
| $Rb_2$ | D-Glucose-($\beta$-1-2)-D-Glucose | L-arabinopyranoside-($\alpha$-1-6)-D-Glucose |
| Rc | D-Glucose-($\beta$-1-2)-D-Glucose | L-arabinofuranoside-($\alpha$-1-6)-D-Glucose |
| Rd | D-Glucose-($\beta$-1-2)-D-Glucose | D-Glucose |

One of the best studied and documented activities of ginseng is its ability to act as a stimulant and anti-fatigue agent. Further studies have also indicated that *Panax ginseng* could increase locomotion activity and modify feline EEG recording. *Panax ginseng's* adaptogenic effects are believed to be due to the action of ginsenosides on the adrenal cortex and on the brain. In 1985, Saito found, from studies with mice and organ cultures, that ginsenoside $Rb_1$ plays an important role in the catecholamine synthesis of catecholaminergic neurons of the brain, in the ganglion and in the chromaffin cells of the adrenal cortex, as well as in the formation of nerve fibers and in the function of the sympathetic nerve endings. The foundation of these various nerve fibers are important in maintaining glucocorticoid secretion, which regulates the bodies ability to deal with stress. $Rg_1$, on the other hand, is believed to play an important role in the memory and in sexual behavior. Also, a significant release of adrenocorticotropic hormone (CTH) by rat pituitary cell cultures was observed after doses of $Rg_1$ by Odani et al. in 1987. Tsang et al. were able to show that a total ginsenoside extract can influence brain functions and behavior patterns.

*Panax ginseng* may also have the ability to enhance the body's natural immune system by increasing the rate of phagocytosis. Several types of white blood cells are generically known as "phagocytes." Phagocytes attack, engulf and release powerful enzymes that destroy invaders in the blood stream, including microorganisms and pathogens through a process referred to as phagocytosis.

*Panax ginseng* plants are treated during their growing season with numerous herbicides and fungicides which ultimately always lead, regardless of their form, to residues in the ginseng product, even though sometimes in minute amounts. These residues are understandably undesireable in every case, as is underlined by the intensive public debate surrounding their use. Raw materials used in the production of medicinal products are especially subject to critical evaluation since medicinal products have proven, on account of the demand for purity, to be a very sensitive consumed substance. Consequently, it would be considered advantageous, if it were possible, to produce medicinal products extracted from natural products, having a very low residue content.

Quintozene is a technical-grade preparation of the chlorinated benzene derivative pentachloronitrobenzene (PCNB). PCNB is used as a herbicide and fungicide for seed and soil treatment, and as a slime inhibitor in industrial waters. PCNB has been found in drinking water, well water, crop land and nursery soils, spinach leaves, cheese, fruits, ground grains, leaf and stem vegetables, nuts, oil seed by-products and more recently in ginseng products. The most probable route of human exposure to PCNB is through the ingestion of contaminated food.

Technical-grade PCNB contains impurities. The specific impurities and their amounts depend on the manufacturer and the manufacturing procedure. The relevant impurities are pentachloroaniline (PCA), pentachlorothioanisole (PCTA), and hexachlorobenzene (HCB), because they have also been recently detected as contaminants of ginseng and because they are metabolites/contaminants of PCNB.

Toxicity of PCNB is observed in animals and humans only at doses in the multiple mg/kg body weight range. The acute lethal dose for humans is estimated to be 500 mg/kg or greater. There is no information available on the long-term health effects of quintozene in humans, but the lowest chronic daily dose found to elicit liver changes of dogs is 4.5 mg/kg/day.

The EPA-established Reference Dose (RfD) for quintozene is 0.003 mg/kg/day. EPA estimates that consumption of this dose or less over a lifetime would not likely result in the occurrence of chronic, noncancer effects. This RfD is based on liver toxicity in dogs, including increased liver weight and effects on liver enzymes. EPA has medium confidence in the RfD because the principal study on which the RfD is based appears to be of fair quality, and because of the lack of a complete database on chronic toxicity. The EPA allowable daily intake (ADI) is 0.007 mg/kg/day, and the allowable daily intake from the UN CODEX Alimentarius is 0.01 mg/kg/day. The health risk posed by any chemical, even a carcinogenic compound, depends on the dose at the target site of action as well as its potency in producing an adverse health effect.

PCNB has been observed to bioaccumulate in tissues only at trace or very low concentrations. Two of its metabolites, PCA and PCTA, likewise do not significantly bioaccumulate in tissues. HCB, on the other hand, has significant bioaccumulation. Early toxicity studies of quintozene (PCNB) attributed toxicity to PCNB; however toxicity was most probably due to the contaminant HCB. It is unclear at this time if HCB contributed to tumor production in PCNB carcinogenicity studies. The reported teratogenic activities of PCNB in mice and rats were also most probably due to contamination with HCB because purified PCNB and PCA were not teratogenic.

A variety of different methods for isolating and purifying nonpolar compounds from natural substances including ginsenosides with the simultaneous separation of undesireable contaminants such as pesticide residues have been published. For example, Forster, et al. in their U.S. Pat. Nos. 4,842,878 and 4,946,695 describe the production of hop extracts with a low content of pesticides from hops which are laden with pesticides. In their process, in a first step, the pesticides and the component materials of the hops are extracted with compressed gases and, in a subsequent step, there is carried out a separation of extract and pesticides with the aid of a solid adsorption agent. However, the supercritical carbon dioxide which is utilized is not an efficient solvent for the ginsenosides. A further disadvantage is the insufficient selectivity of the adsorption agent since, besides the pesticides, desired hop component materials are also adsorbed and thus the yields are reduced.

Furthermore, it is known to remove pesticides from senna leaves with dry, supercritical carbon dioxide in which case the content of chlorinated pesticides is reduced by up to 98% without the polar active materials, the sennosides, being co-extracted. However, the application of the process which is successful in the case of senna leaves to ginseng roots has proved to be impossible. The ginsenosides, regarded as being the active materials, are admittedly not extracted with supercritical carbon dioxide but the chlorinated pesticides are also not removed in a satisfactory manner. Thus, for example, quintozene, which is regarded as being the main contaminant of ginseng roots and thus a leading substance for undesired, lipophilic, chlorinated pesticides, is only reduced to about 30% so that the extracted ginseng roots do not even approach the region of commercial usefulness when the pesticide content exceeds the permitted values.

Schutz, et al., in their U.S. Pat. No. 5,093,123, describe a method of extracting pesticides from ginseng roots using carbon dioxide. However, for this method to function, the moisture content of the roots requires adjustment followed by extracting the moistened root with carbon dioxide at a pressure of more than 100 bar.

The above U.S. Patents, issued to Forster et al. and Schutz et al., are just a couple of examples of the processes that currently exist in the literature, whereby ginsenosides are extracted, isolated and purified from various plant materials. However, each process disclosed involves multiple steps, which require fairly extreme conditions to function and various solvents. Consequently, the disclosed laboratory scale processes are not easily scaled up to an efficient commercial process where disposal considerations of various solvents play an important role in the overall feasibility of the process. A further disadvantage of the processes as disclosed in the literature is the requirement of using super critical $CO_2$ in combination with high pressures.

There is still a need, therefore, for a process and procedure for removing undesireable residues that may be toxic from natural substances that are produced for consumption.

SUMMARY OF THE INVENTION

Accordingly, it is an object of this invention to provide a simplified method for the extraction, isolation, and purification of specific compounds.

Another object of the present invention is to separate, from a mixture of compounds, those compounds that are more polar or less polar than the target compound.

A further object of the invention is to separate ginsenosides from undesired compounds that are more polar or less polar.

Additional objects, advantages, and novel features of this invention shall be set forth in part in the description and examples that follow, and in part will become apparent to those skilled in the to art upon examination of the following or may be learned by the practice of the invention. The objects and the advantages of the invention may be realized and attained by means of the instrumentalities and in combinations particularly pointed out in the appended claims.

To achieve the foregoing and other objects and in accordance with the purposes of the present invention, as embodied and broadly described herein, the method of this invention comprises an extract containing a mixture of compounds having varying polarities that is subsequently fractionated using a series of columns containing an absorbent material.

BRIEF DESCRIPTION OF THE DRAWINGS

The accompanying drawings, which are incorporated in and form a part of the specification, illustrate the preferred embodiments of the present invention, and together with the descriptions serve to explain the principles of the invention. In each of FIGS. 2 and 3, the vertical axis represents the percentage of micrograms of analyte in starting material and the horizontal axis represents the number of column volumes of eluent passed over the column.

In the Drawings.

DETAILED DESCRIPTION OF THE PREFERRED EMBODIMENTS

Figure 1:
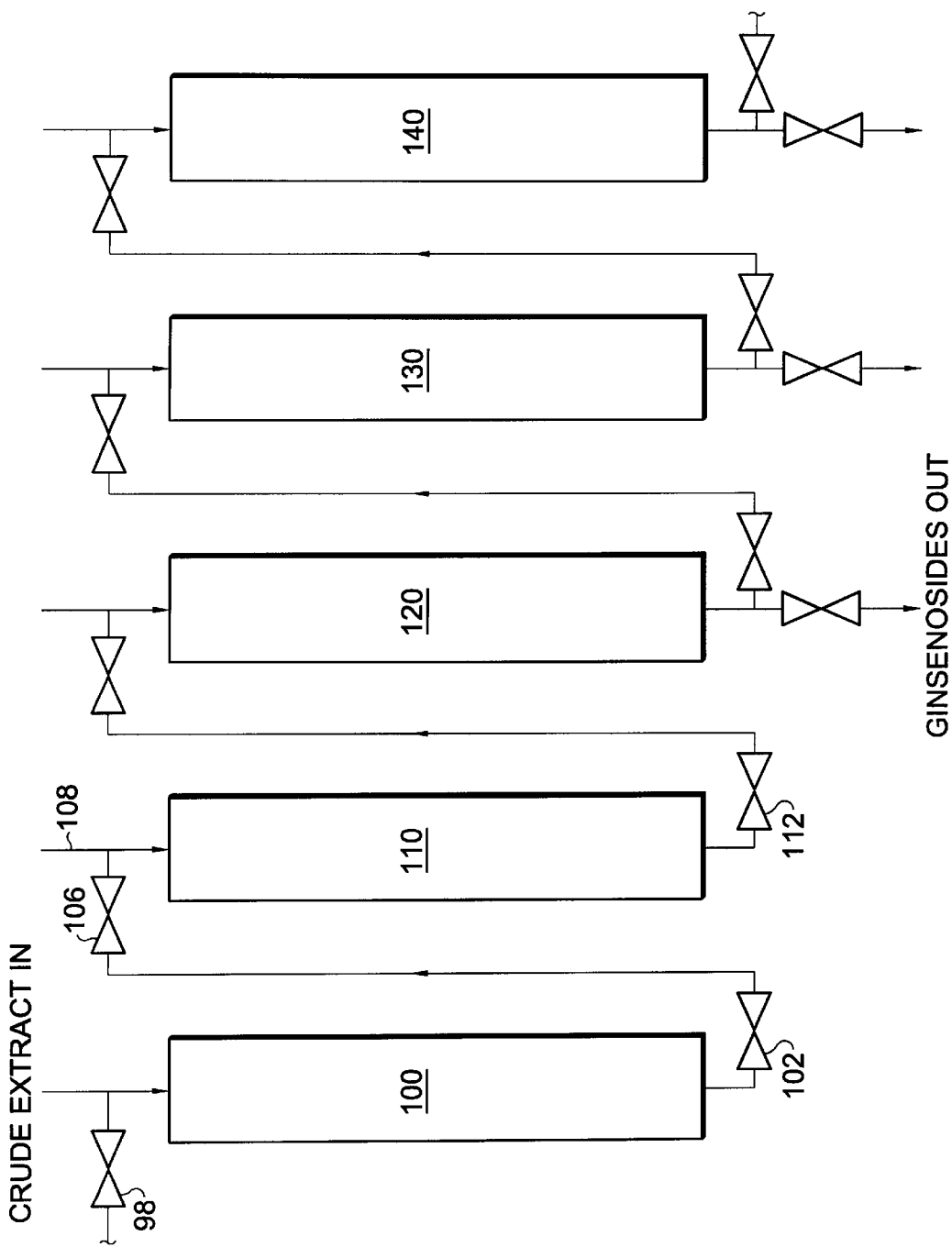
FIG. 1 is a schematic representation of the series of columns used to carry out the method of the present invention.

In general, the present invention relates to a process for the removal of undesireable compounds or residues from an extract which are more polar or less polar than the desired target compound. By way of example, pesticide and fungicide contaminants or residue contaminants are the undesireable compounds that are being removed from an extract of *Panax ginseng* having ginsenosides as the target compounds. However, a *Panax ginseng* extract is named in this connection only by way of example, since the problem of removing undesireable residues occurs in numerous natural substances, whether the starting materials are wild or cultivated. The preferred embodiment of the present invention is a three step process and is described in detail below. The first step includes contacting a plant material that contains the desired target compound(s) with a solvent, thus producing a crude extract containing a mixture of compounds that includes, in addition to the undesireable residues, the desired target compound(s). The second step involves passing the crude extract through a series of columns containing an absorbent that retards the movement of the undesireable compounds, while allowing the desired compounds to pass. The series of columns is critical to the continuous method of the present invention as will be discussed in further detail below. The third and final step involves drying the eluant product to achieve a final product.

This invention includes a process for the extraction of ginsenosides and the removal of undesireable compounds, such as pesticides and fungicides from plant materials or biomasses that contain ginsenosides. As way of illustration only, the following is a partial list of plant sources containing ginsenosides: *Panax ginseng, Panax quinquefolium, Panax japonicum*, and *Panax notoginseng*. Again, this list is exemplary of the plant materials that contain ginsenosides, and is not meant to limit the scope of plant materials which may be utilized by the present invention. It has further been ascertained that the separation of undesireable materials by the method of the invention is also successful with a wide variety of starting materials other than *Panax ginseng*.

For example, undesireable residues that are less polar or more polar than the desired target compound can be removed in accordance with the present invention during the recovery of the following categories of natural substances:

1. vegetable oils, for example, from oil-bearing seeds, seeds and nuts;
2. aromatic and odorous substances, for example, from fruits, vegetables, herbs and tobacco;
3. drugs, for example, from medicinal herbs and roots; and
4. spice extracts, for example, from spice plants such as, vanilla, garlic, pepper and cinnamon.

The first step in the process of the present invention, extraction of the target compounds in this particular instance the target compounds are ginsenosides compounds, is preferably accomplished by mixing or contacting a solvent, such as an alcohol, and preferably ethanol or methanol with a plant material containing ginsenosides. Depending on the type of plant material used, it may be necessary to grind it into a range of 0.1–10 mm. The degree of comminutation of the plant material should provide sufficient particulate surface area for the solvent to contact, but depends on the type of plant material used. The skilled person in this art will recognize that a variety of extraction methods are available in the literature, such as, percolation, vat extraction, countercurrent extraction, etc. The particular method of extraction employed is not essential to the process of the present invention. In the extraction process, the temperature of extraction is between room temperature or about 22° C. to about 70° C., with 50–60° C. being preferred; however, the temperature is not essential to this invention. The amount of plant material to solvent mixture used in the extraction process varies between 1:1 to 1:10 on a gram:milliliter basis, with 1:1 to 1:3 being preferred; however, this mixture is not essential to the invention. The ginsenosides and some of the extraneous materials that are contained in the comminuted plant material are soluble in the solvent used. Thus the solvent, the ginsenosides and some of the extraneous materials including the undesireable residues from fungicides or pesticides form the crude extract. The crude alcohol extract may be diluted with distilled water to a final volume of approximately 40–75% alcohol in water and preferably 55–65% alcohol in water. The resulting solution is then filtered to remove insoluble materials. It has been found that the ratio of solvent to water has a significant effect on the quantity of pesticides that are extracted from the comminuted plant material. That is to say, extraction using 75% and greater alcohol in water, results in a greater extraction of pesticides and ginsenosides, while a 55–65% alcohol in water solvent results in a reduced amount of pesticides and ginsenosides being extracted.

After completion of the formation of the crude extract, the second step, the removal of the undesireable compounds which may be less polar or more polar than the ginsenosides begins. The crude extract contains not only the desired ginsenosides, and the undesireable compounds, but also extraneous plant materials that are soluble in the solvent of the crude extract. It is desirable to remove the undesireable compounds from the crude extract, resulting in the recovery of the ginsenosides and extraneous materials in as close as possible to their natural profile.

To remove the undesireable compounds, the crude extract which may be diluted with water is placed in contact with an absorbent material or matrix. The matrix that is chosen is dependent upon the polarity of the compounds to be separated. Consequently, if the undesireable compounds are more polar than the target compound, a normal phase matrix such as silica gel or fluorasil is used. However, if the undesireable compounds are less polar than the target compound, a reversed phase matrix is used. It should be noted that the process of the present invention is operational only as long as the polarity of the compounds to be separated do not overlap. In this particular embodiment, the undesireable compounds are less polar than the ginsenosides; consequently, the preferred absorbent is a polystyrene resin, such as, XAD-16™, manufactured by Rohm & Haas, or HP 2055 manufactured by Mitsubishi Kasai. Other reversed phase matrixes that can be used but are not limited to, are acrylic resins, such as, ToSoHaas CG-161™, polyamide resins, such as, Polyamide-Nylon 6, or C-18. In general, the crude extract is placed in contact with a matrix that is capable of absorbing the undesireable compounds of a particular polarity. Consequently, those compounds whose polarity do not allow for absorption, are not retained. The container that holds the matrix could be a vat type container with or without a stirrer, a single column or multiple columns; however, the preferred embodiment of the present invention contemplates using a series of columns.

FIG. 1 is illustrative of the series of columns, each of which is properly packed with an absorbent that is used to remove the undesireable compounds present in the crude extract. The columns are prepared in accordance with the resin manufacturer's recommended procedures. Crude extract containing the ginsenosides and some of the extraneous materials, including the undesireable residues from fungicides or pesticides, is continuously loaded onto the first column 100. The crude extract filters down over the absorbent (not shown) until it exits column 100 where it is then directed through columns 110, 120 and 130 by way of a series of pipes and valves. Compounds having a lower affinity for the absorbent, such as the ginsenosides, are specifically desorbed, passing directly through the absorbent at a rate which is greater than the undesireable compounds, which have a greater affinity for the absorbent. Surprisingly and fortunately, the compounds being separated, according to the present invention, do not overlap in polarity, hence allowing for separation.

Since the undesireable compounds have a greater affinity for the absorbent and are retarded by the absorbent, the absorbent slowly becomes "loaded" with undesireable compounds until it is finally spent or exhausted. The data in Table 1 below indicates that column 100 reaches its capacity for retaining undesireable compounds after approximately 20–24 column volumes of crude extract have been loaded. At this point, the original concentration of undesireable compounds in the crude extract is approximately equivalent to the concentration of undesireable compounds eluting out from column 100.

TABLE 1

| Undesireable Compounds | Original Concentration in the Crude Extract | 1st Column 100 Column Volumes | | | | | | |
|---|---|---|---|---|---|---|---|---|
| | | 4 | 8 | 12 | 16 | 20 | 24 | 28 |
| Pentachlorobenzene | 0.15 | nd | nd | nd | nd | nd | 0.00 | 0.01 |
| 2,3,5,6-Tetrachloronitrobenzene | 0.2 | nd | nd | nd | 0.01 | 0.03 | 0.06 | 0.10 |
| 2,3,5,6-Tetrachloroaniline | 0.08 | nd | nd | 0.01 | 0.04 | 0.06 | 0.08 | 0.08 |
| BHC alpha isomer | 0.48 | nd | nd | 0.09 | 0.36 | 0.42 | 0.57 | 0.54 |
| Hexachlorobenzene | 0.25 | nd | nd | nd | nd | nd | nd | nd |
| BHC beta isomer | 0.25 | nd | nd | 0.16 | 0.27 | 0.21 | 0.25 | 0.24 |
| Lindane | 0.38 | nd | nd | 0.16 | 0.38 | 0.37 | 0.47 | 0.42 |
| Pentachloronitrobenzene | 1.68 | nd | nd | nd | nd | 0.02 | 0.04 | 0.11 |
| BHC delta isomer | 0.88 | nd | 0.12 | 0.60 | 1.03 | 0.82 | 0.96 | 0.88 |
| Pentachloroaniline | 1.35 | nd | 0.01 | 0.16 | 0.79 | 1.03 | 1.44 | 1.41 |
| Pentachlorothioanisole | 0.1 5 | nd | nd | nd | nd | nd | nd | nd |
| Total | 5.83 | 0.00 | 0.13 | 1.19 | 2.88 | 2.96 | 3.87 | 3.79 |

All Units are expressed in µg/mL.

Figure 2:
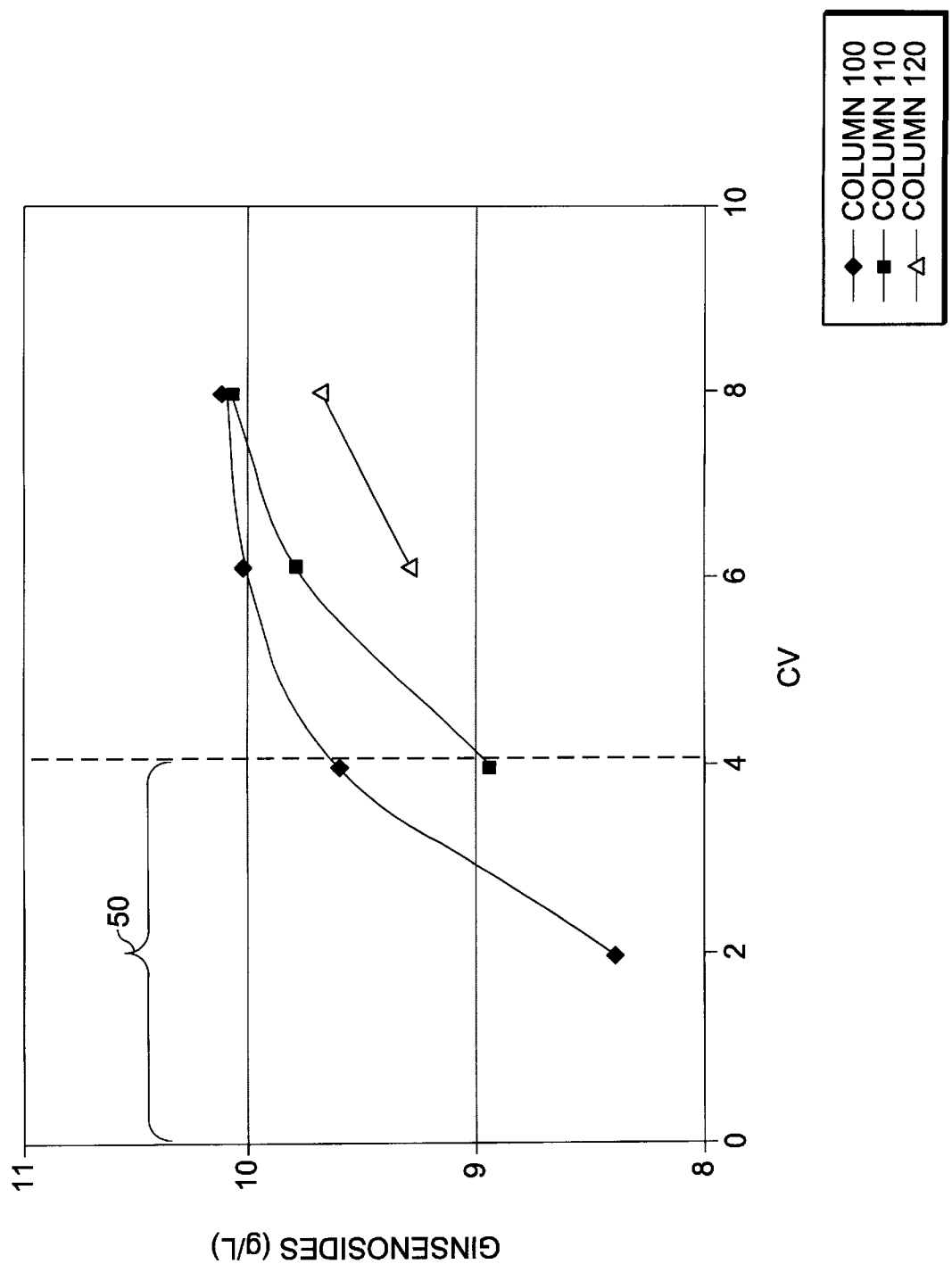
FIG. 2 graphically represents the quantity of ginsenosides per column volume (CV) eluting from columns 1 through 4.
Figure 3:
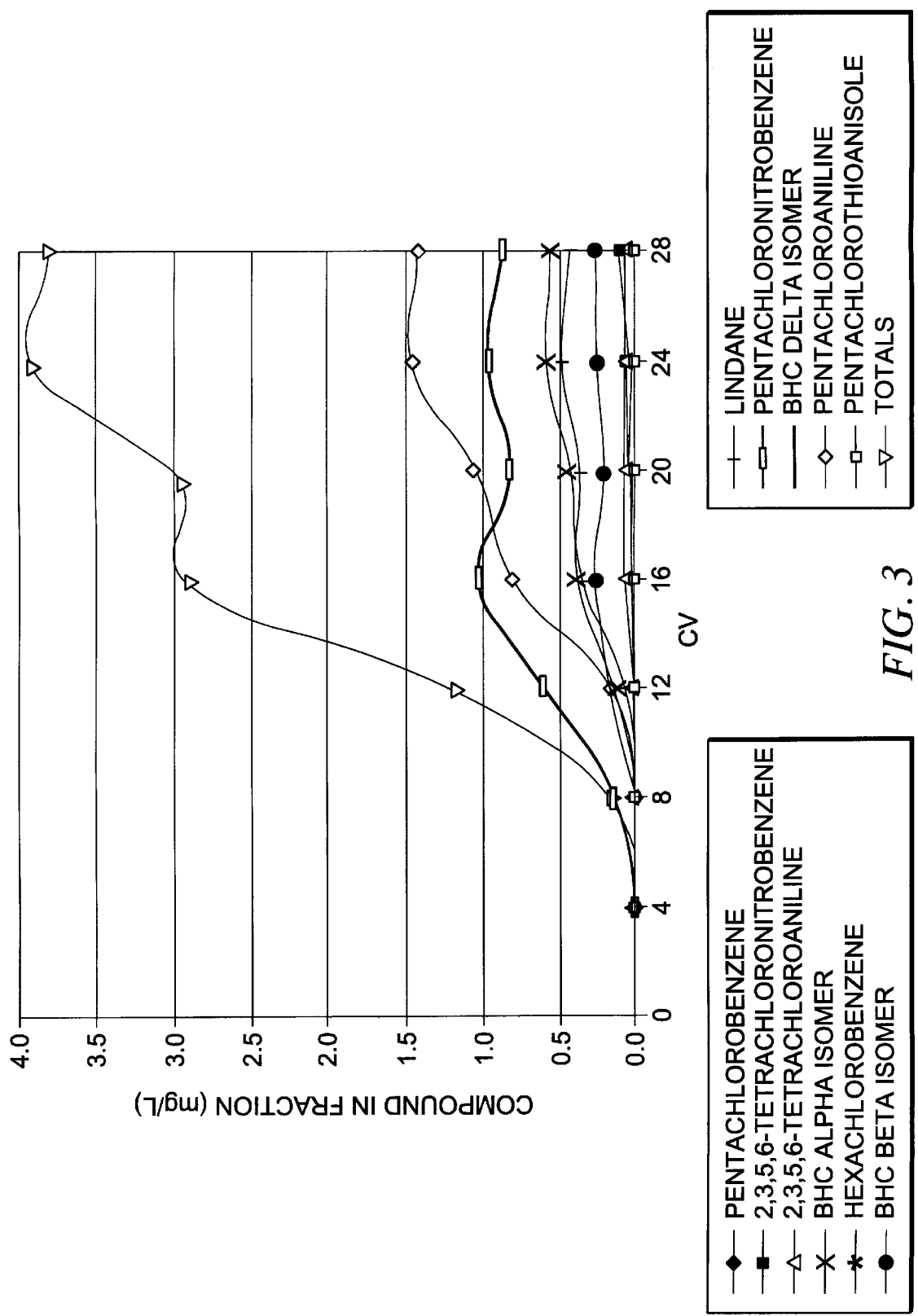
FIG. 3 graphically represents the quantity of pesticides per column volume (CV) eluting from column 1.

Furthermore, the data in Table 1 indicates that no detectable levels of undesireable compounds elute from column 100 until approximately eight column volumes of extract have flowed over the absorbent in column 100. This is a fact that the method of the present invention exploits. Referring now to FIGS. 2 and 3, the ginsenosides (shown in FIG. 2) are eluting from column 100 after only two column volumes of crude extract has flowed over the absorbent while the undesireable compounds (shown in FIG. 3) begin to elute from column 100 after four column volumes. Consequently, the entire crude extract eluting between zero and four column volumes, indicated as area 50, is void of the undesireable compounds, and this entire volume is the desired eluant product. Since this process of the present invention, however, is designed for a commercial plant, efficiency and speed are crucial factors. Thus, the four column volumes are not immediately collected as they elute from column 100. Instead, the crude extract less the undesireable compounds is immediately directed towards column 110 which was prepared in the same manner as column 100. Again, referring to FIG. 2, the ginsenosides are eluting from column 110 after four column volumes. However, as indicated in Table 2 below, the undesireable compounds do not begin to elute from column 110 until approximately fourteen column volumes have eluted.

TABLE 2

| Undesireable Compounds | Original Concentration in the Crude Extract | 2nd Column 110 Column Volumes | | | | | |
|---|---|---|---|---|---|---|---|
| | | 10 | 14 | 18 | 22 | 26 | 28 |
| Pentachlorobenzene | 0.15 | nd | nd | nd | nd | nd | nd |
| 2,3,5,6-Tetrachloronitrobenzene | 0.2 | nd | nd | nd | nd | nd | nd |
| 2,3,5,6-Tetrachloroaniline | 0.08 | nd | nd | nd | 0.004 | 0.01 | 0.02 |
| BHC alpha isomer | 0.48 | nd | nd | nd | nd | 0.06 | 0.15 |
| Hexachlorobenzene | 0.25 | nd | nd | nd | nd | nd | nd |
| BHC beta isomer | 0.25 | nd | nd | nd | 0.08 | 0.20 | 0.30 |
| Lindane | 0.38 | nd | nd | nd | nd | 0.16 | 0.30 |
| Pentachloronitrobenzene | 1.68 | nd | nd | nd | nd | nd | nd |
| BHC delta isomer | 0.88 | nd | 0.01 | 0.07 | 0.38 | 0.79 | 1.20 |
| Pentachloroaniline | 1.35 | nd | 0.004 | 0.004 | 0.01 | 0.08 | 0.25 |
| Pentachlorothioanisole | 0.15 | nd | nd | nd | nd | nd | nd |
| Total | 5.83 | 0.00 | 0.02 | 0.08 | 0.48 | 1.30 | 2.22 |

All Units are expressed in $\mu$g/mL.

As discussed above, the crude extract less the undesireable compounds eluting from column 110 is directed into a third column 120. Again, referring to FIG. 2, the ginsenosides are eluting from column 120 by six column volumes. However, as indicated below in Table 3, up to twenty-eight column volumes elute from column 120 before any undesireable compounds are detected.

TABLE 3

| Undesireable Compounds | Original Concentration in the Crude Extract | 3rd Column 120 Column Volumes | Product Pool |
|---|---|---|---|
| | | 10 | 28 |
| Pentachlorobenzene | 0.15 | nd | nd |
| 2,3,5,6-Tetrachloronitrobenzene | 0.2 | nd | nd |
| 2,3,5,6-Tetrachloroaniline | 0.08 | nd | nd |
| BHC alpha isomer | 0.48 | nd | nd |
| Hexachlorobenzene | 0.25 | nd | nd |
| BHC beta isomer | 0.25 | nd | nd |
| Lindane | 0.38 | nd | nd |

TABLE 3-continued

| Undesireable Compounds | Original Concentration in the Crude Extract | 3rd Column 120 Column Volumes | Product Pool |
|---|---|---|---|
| | | 10 | 28 |
| Pentachloronitrobenzene | 1.68 | nd | nd |
| BHC delta isomer | 0.88 | nd | nd |
| Pentachloroaniline | 1.35 | nd | nd |
| Pentachlorothioanisole | 0.15 | nd | nd |
| Total | 5.83 | 0.00 | 0.00 |

All Units are expressed in $\mu$g/mL.

Three critical advances are achieved with the method of the present invention disclosed herein. First, as the crude extract passes through the additional media, a greater degree of separation is achieved between the desired target compound, that is the ginsenosides in this case, and the undesireable compounds, that is the pesticides. Second, as a result of creating a higher degree of separation between the desired and undesireable compounds, it is possible to collect a higher percentage of the desired compounds. Finally, by running the crude extract through a series of columns all connected in a cyclical fashion, columns that are spent can be removed from the series, washed, repacked with absorbent and replaced into the process without any down time.

For example, as discussed previously, the first column 100 is spent or exhausted after approximately twenty-four column volumes has passed over the column. Consequently, valves 98 and 102 can be closed, allowing for the removal and reconstitution of column 100. While column 100 is being reconstituted, the crude extract formed during the first step is redirected to enter column 110 through pipe 108. Then, when column 110 is spent, valves 106 and 112 are closed, allowing for the cleaning and reconstitution of column 110. This procedure continues down the line until extract eluting from column 140 is directed to freshly constituted column 100. This cyclical pattern is extremely advantageous in a commercial setting because it alleviates the need to take the entire process off-line while one column is being reconstituted and it allows the matrix to be completely exhausted.

The preferred third and final step in the process is the drying of the final product. An appropriate amount of excipient, such as but not limited to, maltodextrin, dicalcium phospate (DCP) or tricalcium phosphate (TCP), is added to the product from step two, thus bringing the ginsenosides to the 7% level and the product is dried on to this excipient, using a rotary evaporator, spray drier, lyophilizer or any other appropriate drying device.

In an alternate embodiment, subsequent to comminutation, the ground biomass can be subjected to an initial wash with an appropriate solvent such as hexane, heptane, MTBE, acetone, or an alcohol such as ethanol to remove the desired pesticides while retaining the desired extractables. This extraction may need to be done at some temperature other than at room temperature. Following this wash the biomass was extracted as usual to recover the desired extractables. This step can be repeated as often as needed. Ginseng biomass with quintozene at 10.6 ppm was ground in a Wiley mill and then extracted three times with hexane which lowered the pesticide level in the biomass to 0.7 ppm.

In a third embodiment, dried ginseng extract produced after the first step of the preferred embodiment containing 17.4 ppm quintozene was supercritically extracted with $CO_2$ which lowered the pesticide to 12.0 ppm in one experiment.

In a fourth embodiment, an alcohol/water extract of an herbal or an alcohol/water solution containing the herbal extractables can be liquid/liquid extracted with a non-polar solvent such as but not limited to hexane, heptane, MTBE, or ether. This extraction can be repeated as often as needed. An ethanol/water solution of ginseng extractables containing 18.3 ppm quintozene was extracted three times with heptane reducing the fungicide to 1.55 ppm in one experiment.

In the fifth embodiment, an alcohol/water extract of an herbal or an alcohol/water solution containing the herbal extractables can be contacted with an absorbent form of carbon. After the carbon is removed, it should be thoroughly washed to optimize *Panax ginseng* recovery. This step can be repeated as often as needed. This approach, using Carbograph™ manufactured by Phenomenex, reduced the quintozene in ginseng from 18.3 ppm to 0.92 ppm in one experiment.

The foregoing description is considered as illustrative only of the principles of the invention. Furthermore, since a number modifications and changes will readily occur to those skilled in the art, it is not desired to limit the invention to the exact construction and process shown described above. Accordingly, all suitable modifications and equivalents may be resorted to falling within the scope of the invention as defined by the claims which follow.

What is claimed is:

1. A method of isolating target compounds free of impurities from a plant material extract, wherein the isolated target compounds retain the natural chemical profile of the plant material extract, wherein said impurities are pesticides, herbicides, fungicides, metabolites of pesticides, or a combination thereof and said impurities are either more or less polar than said target compounds, said method comprising:

(a) preparing a crude extract of said plant material, wherein said crude extract comprises said target compounds and said impurities;

(b) preparing a series of columns comprising two or more columns, each of said columns containing the same type of an absorbent material, wherein said columns in said series are sequentially connected in a cyclical manner and wherein said absorbent material selectively absorbs said impurities but does not absorb said target compounds;

(c) continually passing said crude extract through a first column in said series of columns to provide a first eluent, until a first preselected amount of said impurities is detected in said first eluent, wherein said first eluent comprises said target compounds and an amount of said impurities that is less than the amount of impurities in said crude extract;

(d) continually directing said first eluent from step (c) to an adjacent column in said series of columns;

(e) continually passing said first eluent through said adjacent column to provide a second eluent, until a second preselected amount of impurities is detected in said second eluent; and (f) repeating steps (d)–(e) as necessary until said target compounds free of said impurities are isolated.

2. The method of claim 1, wherein said impurities are less polar than said target compounds and said absorbent material is a reversed phase matrix.

3. The method of claim 2, wherein said reversed phase matrix is selected from the group consisting of polystyrene resins, acrylic resins and polyamide resins.

4. The method of claim 1, wherein said impurities are more polar than said target compounds and said absorbent material is a normal phase matrix.

5. The method of claim 4, wherein said normal phase matrix is selected from the group consisting silica gel and fluorasil.

6. The method of claim 1, wherein said plant material is selected from the group consisting of *Panax ginseng, Panax quinquefolium, Panax japonicum* and *Panax notoginseng.*

7. The method of claim 1, wherein said target compounds comprise ginsenosides.

8. The method of claim 1, further comprising washing said plant material with a solvent prior to preparing said crude extract.

9. The method of claim 1, further comprising performing a supercritical extraction of said plant material with carbon dioxide prior to preparing said crude extract.

10. The method of claim 1, wherein said crude extract is prepared by mixing said plant material with a solvent comprising at least 75% alcohol.

11. The method of claim 1, further comprising washing said crude extract with a nonpolar solvent prior to loading said crude extract onto said first column.

12. The method of claim 1, further comprising contacting said crude extract with an absorbent form of carbon prior to loading said crude extract onto said first column.

13. The method of claim 1, further comprising, after step (d), removing said first column, cleaning said absorbent in said first column to provide a reconstituted column, and connecting said reconstituted column to a last column in said series of columns.

14. The method of claim 1, further comprising mixing said isolated target compounds with an excipient and drying said mixture.

15. The method of claim 1, wherein said impurities are selected from the group consisting of pentachlorobenzene, 2, 3, 5, 6-tetrachloronitrobenzene, 2, 3, 5, 6-tetrachloroanaline, 1, 2, 3, 4, 5, 6-hexachlorocyclohexane, hexachlorobenzene, lindane, pentachloronitrobenzene, and pentachloroanaline, pentachlorothioanisole.

16. A method of isolating ginsenosides free of impurities from a plant material extract, wherein the isolated ginsenosides retain the natural chemical profile of the plant material extract, wherein said impurities are pesticides, herbicides, fungicides, metabolites of pesticides, or a combination thereof, and said impurities are either more or less polar than said ginsenosides, said method comprising:

(a) preparing a crude extract of said plant material, wherein said crude extract comprises said ginsenosides and said impurities;

(b) preparing a series of columns comprising two or more columns, each of said columns containing the same type of an absorbent material, wherein said columns in said series are sequentially connected in a cyclical manner and wherein said absorbent material selectively absorbs said impurities but does not absorb said ginsenosides;

(c) continually passing said crude extract through a first column in said series of columns to provide a first eluent, until a first preselected amount of said impurities is detected in said first eluent, wherein said first eluent comprises said ginsenosides and an amount of said impurities that is less than the amount of said impurities in said crude extract;

(d) continually directing said first eluent from step (c) to an adjacent column in said series of columns;

(e) continually passing said first eluent through said adjacent column to provide a second eluent, until a second preselected amount of impurities is detected in said second eluent; and (f) repeating steps (d)–(e) as necessary until said ginsenosides free of said impurities are isolated.

17. The method of claim 16, wherein said plant material is selected from the group consisting of *Panax ginseng, Panax quinquefolium, Panax japonicum* and *Panax notoginseng*.

18. The method of claim 16, further comprising, after step (d), removing said first column, cleaning said absorbent in said first column to provide a reconstituted column, and connecting said reconstituted column to a last column in said series of columns.

19. The method of claim 16, wherein said absorbent material is a reversed phase matrix is selected from the group consisting of polystyrene resins, acrylic resins and polyamide resins.

20. The method of claim 16, wherein said impurities are selected from the group consisting of pentachlorobenzene, 2, 3, 5, 6-tetrachloronitrobenzene, 2, 3, 5, 6-tetrachloroanaline, 1, 2, 3, 4, 5, 6-hexachlorocyclohexane, hexachlorobenzene, lindane, pentachloronitrobenzene, and pentachloroanaline, pentachlorothioanisole.

21. A method of isolating ginsenosides free of impurities from a plant material extract, wherein said plant material is *Panax ginseng, Panax quinquefolium, Panax japonicum* or *Panax notoginseng*, wherein said ginsenosides retain the natural chemical profile of the plant material extract, and wherein said impurities are pesticides, herbicides, fungicides, metabolites of pesticides, or a combination thereof, said impurities being less polar than said ginsenosides, said method comprising:

(a) preparing a crude extract of said plant material, wherein said crude extract comprises said ginsenosides and said impurities;

(b) preparing a series of columns comprising two or more columns, each of said columns containing the same type of a reversed phase matrix, wherein said columns in said series are sequentially connected in a cyclical manner and wherein said reversed phase matrix selectively absorbs said impurities but does not absorb said ginsenosides;

(c) continually passing said crude extract through a first column in said series of columns to provide a first eluent until a first preselected amount of said impurities is detected in said first eluent, wherein said first eluent comprises said ginsenosides and an amount of said impurities that is less than the amount of said impurities in said crude extract;

(d) continually directing said first eluent from step (c) to an adjacent column in said series of columns;

(e) continually passing said first eluent through said adjacent column to provide a second eluent, until a second preselected amount of impurities is detected in said second eluent; and (f) repeating steps (d)–(e) as necessary until said ginsenosides free of said impurities are isolated.

22. The method of claim 21, wherein said impurities are selected from the group consisting of pentachlorobenzene, 2, 3, 5, 6-tetrachloronitrobenzene, 2, 3, 5, 6-tetrachloroanaline, 1, 2, 3, 4, 5, 6-hexachlorocyclohexane, hexachlorobenzene, lindane, pentachloronitrobenzene, and pentachloroanaline, pentachlorothioanisole.

* * * * *